United States Patent
Gavas et al.

(10) Patent No.: US 11,076,796 B2
(45) Date of Patent: Aug. 3, 2021

(54) METHOD AND SYSTEM FOR DETERMINING INACTIVE STATE AND ITS IMPLICATION OVER COGNITIVE LOAD COMPUTATION OF A PERSON

(71) Applicant: Tata Consultancy Services Limited, Mumbai (IN)

(72) Inventors: Rahul Dasharath Gavas, Kolkata (IN); Rajat Kumar Das, Kolkata (IN); Pratyusha Das, Kolkata (IN); Debatri Chatterjee, Kolkata (IN); Aniruddha Sinha, Kolkata (IN)

(73) Assignee: TATA CONSULTANCY SERVICES LLC, Mumeai (IN)

( * ) Notice: Subject to any disclaimer, the term of this patent is extended or adjusted under 35 U.S.C. 154(b) by 943 days.

(21) Appl. No.: 15/726,559

(22) Filed: Oct. 6, 2017

(65) Prior Publication Data

US 2018/0098710 A1   Apr. 12, 2018

(30) Foreign Application Priority Data

Oct. 7, 2016 (IN) .............................. 201621034485

(51) Int. Cl.
*A61B 5/369* (2021.01)
*A61B 5/0533* (2021.01)
(Continued)

(52) U.S. Cl.
CPC ............ *A61B 5/369* (2021.01); *A61B 5/0533* (2013.01); *A61B 5/1118* (2013.01); *A61B 5/165* (2013.01);
(Continued)

(58) Field of Classification Search
CPC ....... A61B 5/369; A61B 5/163; A61B 5/7264; A61B 5/16; A61B 5/053
See application file for complete search history.

(56) References Cited

U.S. PATENT DOCUMENTS

| | | | |
|---|---|---|---|
| 2007/0173699 A1 | 7/2007 | Mathan et al. | |
| 2007/0236488 A1 | 10/2007 | Mathan et al. | |
| 2011/0207099 A1 | 8/2011 | Chen et al. | |

OTHER PUBLICATIONS

P. Das, D. Chatterjee, A. Ghose and A. Sinha, "A system for remote monitoring of mental effort," 2016 IEEE 6th International Conference on Consumer Electronics—Berlin (ICCE-Berlin), Berlin, 2016, pp. 222-226, doi: 10.1109/ICCE-Berlin.2016.7684760. (Year: 2016).*

(Continued)

*Primary Examiner* — Daniel L Cerioni
*Assistant Examiner* — Yasmeen S Warsi
(74) *Attorney, Agent, or Firm* — Finnegan, Henderson, Farabaw, Garrett & Dunner LLP (57) ABSTRACT

A method and system for determining cognitive load of a person using a modified baseline is provided. The person is asked to perform a series of activities including staying in eye closed rest state and baseline state and performing a trial state. Simultaneously, EEG signal and GSR signal of the person are captured. The EEG signal and the GSR signal are preprocessed and segmented. The EEG and GSR signals are then used to determine a first set and a second set of inactive states from the baseline interval and the rest interval. The most inactive window is then identified out of the first set of inactive states. The most inactive window is determined from the rest interval of the person. The inactive window is used as the modified baseline to measure the cognitive load of the person.

10 Claims, 5 Drawing Sheets

(51) Int. Cl.
*A61B 5/318* (2021.01)
*A61B 5/349* (2021.01)
*A61B 5/374* (2021.01)
*A61B 5/11* (2006.01)
*A61B 5/16* (2006.01)
*A61B 5/00* (2006.01)

(52) U.S. Cl.
CPC .............. *A61B 5/318* (2021.01); *A61B 5/349* (2021.01); *A61B 5/374* (2021.01); *A61B 5/6801* (2013.01); *A61B 5/7264* (2013.01)

(56) References Cited

OTHER PUBLICATIONS

Anderson, Erik & Potter, Kristin & Matzen, Laura & Shepherd, Jason & Preston, Gilbert & Silva, Claudio. (2011). A User Study of Visualization Effectiveness Using EEG and Cognitive Load.. Comput. Graph. Forum. 30. 791-800. (Year: 2011).*

Lorens Jr, Stanley A., and Chester W. Darrow. "Eye movements, EEG, GSR and EKG during mental multiplication." Electroencephalography & Clinical Neurophysiology (1962). (Year: 1962).*

* cited by examiner

METHOD AND SYSTEM FOR DETERMINING INACTIVE STATE AND ITS IMPLICATION OVER COGNITIVE LOAD COMPUTATION OF A PERSON

PRIORITY CLAIM

This U.S. patent application claims priority under 35 U.S.C. § 119 to India Application No. 201621034485, filed on Oct. 7, 2016. The entire contents of the aforementioned application are incorporated herein by reference.

TECHNICAL FIELD

This disclosure relates generally to the field of cognitive load measurement. More particularly, but not specifically, the invention provides a system and method for measuring cognitive load of a person using a modified baseline by determining the inactive or less attentive state of mind for the person, during a task.

BACKGROUND

The study of emotions in human-computer interaction has increased in recent years for variety of purposes. The study of emotions has led to a growing need for computer applications to detect cognitive load experienced by an individual. The cognitive load has been used in a variety of fields that deal with the human mind interacting with some external stimulants. Cognitive load can be defined as the mental effort required for a particular person to comprehend or learn some material, or complete some task. Cognitive load is relative to both the user and the task being completed, at any single point in time.

There are different approaches for measuring the cognitive load of a person. Most of the approaches use physiological signal of the person to measure the cognitive load. Electroencephalogram (EEG) signals are used to analyze the brain signals to measure the cognitive load for the individual. The most reported works indicate that alpha and theta frequency bands are the most dominating ones for different levels of cognitive load. More specifically, alpha frequency band power decreases and theta frequency band power increases with increased cognitive load. The cognitive load was assessed using the alpha-theta information with respect to the baseline activity. Cognitive load analysis mainly focuses on the shift from the baseline information by assuming the baseline to be a state of inactivity. However, it is difficult to ensure that the participant is inactive during wakeful baseline period. So techniques to detect inactivity are crucial in this regard. Conventional methods for measurement of cognitive load using EEG signals use a supervised approach. The methodology of using the EEG signals for measurement of the cognitive load may include issues related to change in intensity and signal range for a same individual for different trials. Also, the EEG signals may vary due to spatial shift in the positioning of the leads from one trial to another for the same individual.

Since the brain is the source of all cognitive activities, it is possible to assess the different states of cognition with appropriate non-invasive physiological sensing tools. The monitoring of workload imposed on the brain gives a better insight while analyzing various mental states. Mental workload or the cognitive load refers to the amount of demands imposed on the working memory during various instruction processing like problem solving, thinking, perception etc.

It is to be noted that alpha activity decreases with drowsiness, sleep and working, but increases with rest. The change in these band energies is evident when the brain switches from the rest to mental working state. Even electro dermal activity is a good indicator of cognitive load. The time-frequency domain statistical parameters of GSR signals are used as the metrics to get an insight of the cognitive load. Other physiological changes used to assess the cognitive load are from heart rate, eye tracking, functional magnetic resonance etc. The mass-acceptance of these modalities is largely dependent on the cost and portability of these sensor devices. Major issues pertaining to the assessment of cognitive load with these devices lies in the resolution of the sensors and the nature of the baseline data used as reference.

The analysis of physiological signals for assessment of cognitive load demands continuous processing at runtime. The existing assessment process expects same level of involvement from the participants, throughout the entire duration of a particular type of task. In reality, this is difficult to achieve due to the inherent inactivity state, hence poses a major challenge in detecting the cognitive load.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In view of the foregoing, an embodiment herein provides a system for determining the cognitive load of a person using a modified baseline. The system comprises an input/output interface, an EEG sensor, a GSR sensor, a preprocessor, a memory and a processor. The input/output interface instructs a person to stay in a rest state, stay in a baseline state and carry out a trial state respectively. The task is performed by the person during the trial state. The EEG sensor senses an EEG signal of the person. The GSR sensor senses a GSR signal of the person. The preprocessor preprocesses the EEG signal and the GSR signal. The processor coupled with the memory. The processor further configured to perform the steps of: segmenting the preprocessed EEG signal and the preprocessed GSR signal in to a rest interval corresponding to the rest state, a baseline interval corresponding to the baseline state and a trial interval corresponding to the trial state; performing power spectral analysis of the EEG signal to determine a first set of inactive states of the person from the baseline interval and the rest interval; identifying a most inactive window out of the first set of inactive states, wherein the most inactive window is during the rest interval of the person; and determining the cognitive load of the person using the EEG signal of the person during the trial state and by using the most inactive window as the modified baseline. The system further configured to validate the identification of the first inactive window by following the steps of: performing power spectral analysis of the GSR signal to determine a set of second inactive states of the person from the baseline interval and the rest interval; identifying a most inactive window out of the set of second inactive states, wherein the most inactive window is during the rest interval of the person; and validating the most inactive state derived from the EEG signal with respect to the most inactive state derived from the GSR signal. According to another embodiment the system also configured to validate that the cognitive load derived from EEG using this most inactive window derived from the first set of inactive states, for both the trials, the high load and the low should follow the same trend as GSR spectral power derived from trial states while comparing with the most inactive window derived from the second set of inactive states.

Another embodiment provides a method for determining the cognitive load of a person using a modified baseline. Initially, a person is instructed to stay in a rest state, stay in a baseline state and carry out a trial state respectively, wherein, a task is performed by the person during the trial state. At next step, an EEG signal of the person is sensed using the EEG sensor and a GSR signal of the person is sensed using the GSR sensor. In the next step, the EEG signal and the GSR signal are preprocessed using a preprocessor. In the next step, the preprocessed EEG signal and the preprocessed GSR signal are segmented in to a rest interval corresponding to the rest state, a baseline interval corresponding to the baseline state and a trial interval corresponding to the trial state. Further, the power spectral analysis of the EEG signal is performed to determine a first set of inactive states of the person from the baseline interval and the rest interval. In the next step, a most inactive window out of the first set of inactive states is identified. The most inactive window is during the rest interval of the person. And finally, the cognitive load of the person is determined using the EEG signal of the person during the trial state and by using the most inactive window as the modified baseline. According to another embodiment the method also comprising validating the identification of the first inactive window. Initially, power spectral analysis of the GSR signal is performed to determine a set of second inactive states of the person from the baseline interval and the rest interval. In the next step a most inactive window is identified out of the set of second inactive states. The most inactive window is during the rest interval of the person. And finally the most inactive state derived from the EEG signal is validated with respect to the most inactive state derived from the GSR signal. According to another embodiment the method further comprising validating the computation of cognitive load using the most inactive window from EEG during both the trials (high load task and the low load task), with the similar information obtained from the GSR signal.

BRIEF DESCRIPTION OF THE DRAWINGS

The embodiments herein will be better understood from the following detailed description with reference to the drawings, in which.

DETAILED DESCRIPTION

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Figure 1:
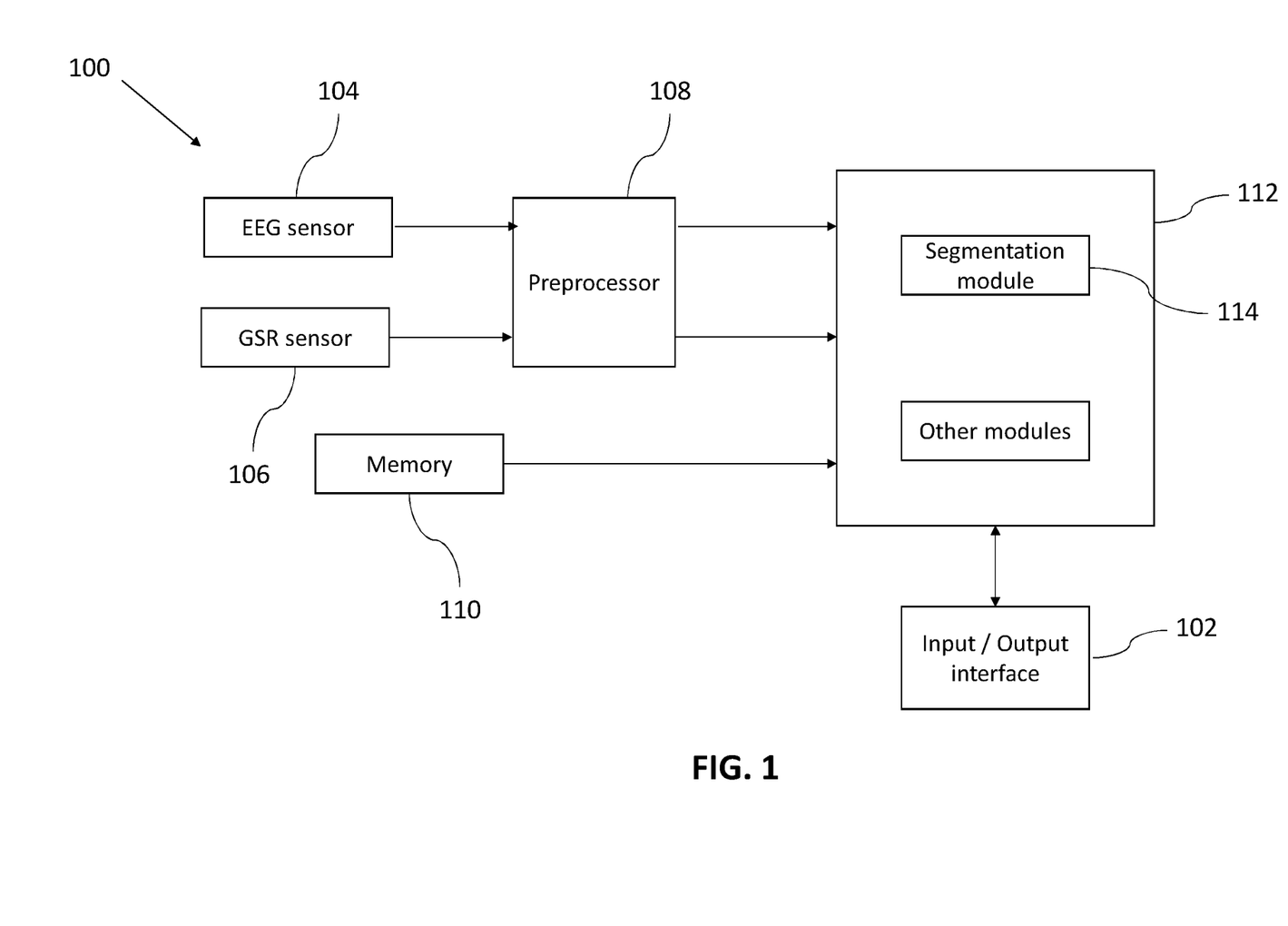
FIG. 1 illustrates a block diagram of a system for determining the cognitive load of a person using a modified baseline, in accordance with an embodiment of the disclosure.

Referring now to the drawings, and more particularly to FIG. 1, where similar reference characters denote corresponding features consistently throughout the figures, there are shown preferred embodiments and these embodiments are described in the context of the following exemplary system and/or method.

According to an embodiment of the disclosure, a system 100 for determining the cognitive load of a person using a modified baseline is shown in the block diagram of FIG. 1. The disclosure provides a method and system to enhance the accuracy of the cognitive load measurement, by determining the inactive or less attentive state of mind for the person, during a task. The system involves the determination of active and inactive state of the person when the person is performing the task. In addition to that, the physiological data is also obtained from the person while performing the task, which can further be used to measure the cognitive load of the person.

The system 100 involves detection of the inactive state of the person during the task. Further its applicability in the assessment of cognitive load (CL) is shown. Initially the alpha activity in the 'conscious rest' or the 'wakefulness rest' with the eyes closed condition were analyzed, since alpha activity is the hallmark in distinguishing the inactive state with the active state. Then the detection of inactivity and working states is validated using a metric designed using alpha and theta band powers. The rest and the working states were evaluated by using Galvanic Skin Response (GSR) along with Electroencephalogram (EEG) signals.

According to an embodiment of the disclosure, a block diagram of the system 100 is shown in FIG. 1. The system 100 includes an input/output interface 102, an electroencephalogram (EEG) sensor 104, a galvanic skin response (GSR) sensor 106, a preprocessor 108, memory 110 and a processor 112 in communication with the memory 110. The memory 110 is configured to store a plurality of algorithms. The processor 112 further includes a plurality of modules for performing various functions. The plurality of modules access the plurality of algorithms stored in the memory 110 to perform various functions.

According to an embodiment of the disclosure, the person is asked to perform a particular task using the input/output interface 102. The input/output interface 102 may include but not limited to a keyboard, a display device, or any other form of communication device. It should be appreciated that in another example, the person may also be instructed by a caregiver to perform certain tasks. In an example, the person is asked to stay in a rest state, stay in a baseline state and carry out a trial state respectively in that order. The task is performed by the person during the trial state. This task is used as stimulus for the person.

Figure 2:
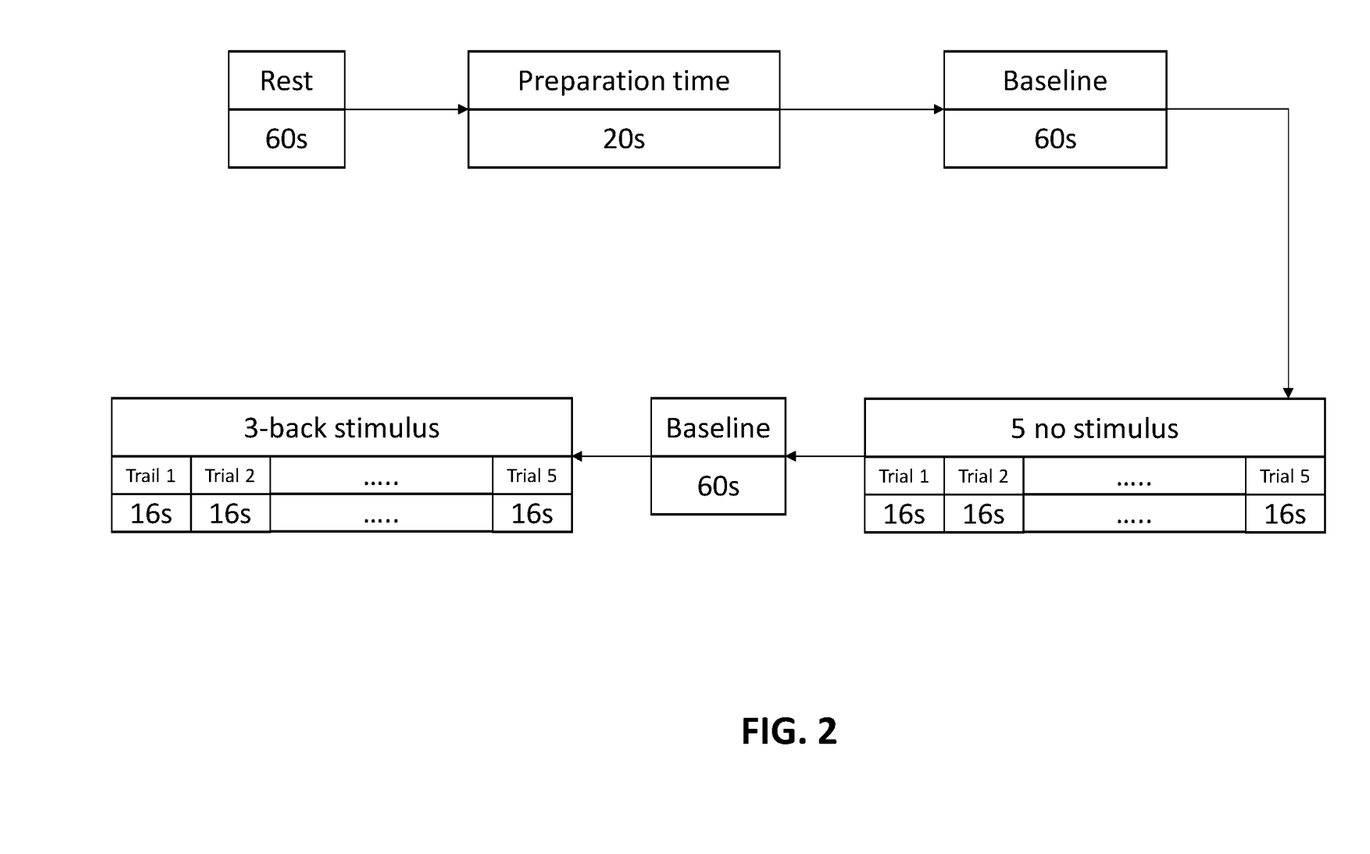
FIG. 2 illustrates a sequence of activities to be performed by the person in accordance with an embodiment of the present disclosure.

According to an embodiment of the disclosure, the sequence of tasks is shown in FIG. 2. The system 100 may use two stimuli, i.e. a 5-number test stimulus and a 3-back memory test. In the 5-number test stimulus, a set of numbers are shown to the person/participants and they are asked to click on the occurrence of number 5. The other stimulus is 3-back memory test where the person are supposed to click on the screen when the current number matches with the one from 3 slides earlier in the sequence. The 5-number test is easier to complete, hence is expected to induce low cognitive load. On the other hand, 3-back memory test is relatively harder and is expected to induce comparatively higher load. The detailed sequence of tasks for rest, baseline and stimuli is shown in FIG. 2. Initially, the person is asked to rest with his/her eyes closed for a period of 60 seconds. Then they are given 20 seconds time to get ready for the stimulus. Then a baseline with a black screen with white fixation cross in the middle is shown for a period of 60 seconds. This is followed with the 5 number stimulus comprising of 5 trials. Then the baseline screen is shown again for 60 seconds. Next, the 3-back stimulus is shown with 5 trials. In both the stimulus, for a particular trial, each number slide is presented for a duration of 1.6 sec; and in each trial, there are 10 slides. During the data logging, markers are inserted to indicate the start of each slide. It should be appreciated that the task is designed in such a way that one stimulus test is of low load as compared to the other stimulus test. In the present example, 5-number test is low load and the 3 back test is high load test. It should also be appreciated that the use of any other method for providing stimulus during the trial state is well within the scope of this disclosure.

According to an embodiment of the disclosure, the system 100 is configured to obtain the EEG signal and the GSR signal of the person, while the person is in rest state, a baseline state or carrying out the task. The EEG signal of the person is obtained using the EEG sensor 104. The EEG signal is collected using a single-channel, dry sensor based headband from Neurosky. It is placed on the FP1 position with grounding at left earlobe as reference. It uses a component called ThinkGear to transfer the data with sampling frequency of 512 Hz. The device renders good usability index. The system 100 further configured to obtain the GSR signal of the person using the GSR sensor 106. The GSR sensor 106 from eSense was used for this purpose. This device applies a very low amount of voltage between index finger and middle finger of the medial phalanges. The GSR sensors are put on the ring and the middle fingers of the left hand. For better connectivity and to capture even smallest changes in the skin conductance level, the gel-based disposable ECG electrodes was used instead of Velcro electrodes. The GSR signal logging is done at a sampling rate of 5 Hz. The EEG and GSR signal are captured in two different devices where the maximum time lag is ensured within ±1 sec. However, this error is negligible owing to the slow varying nature of the GSR. Further, it should also be appreciated that GSR signal takes 3-5 seconds time to reflect mental states. This time difference is also considered while validating information derived from the EEG signal using the GSR signal.

According to an embodiment of the disclosure, the system 100 further includes the preprocessor 108 to preprocess the EEG signal and the GSR signal. The pre-processing of EEG signal is performed to remove the noise, eye-blink and muscle artifacts. The detection of noisy windows are done using the skewness based statistical method. The eye blink detection is done by using the autocorrelation based method and then the signal is filtered. In order to use the GSR signal, an initial screening for the stabiles/labiles are done.

According to an embodiment of the disclosure, the processor 112 includes a segmentation module 114. The segmentation module 114 is configured to segment the preprocessed EEG signal and the preprocessed GSR signal segmented into a rest interval corresponding to the rest state, a baseline interval corresponding to the baseline state and a trial interval corresponding to the trial state with reference from the meta-data markers. Finally, these intervals for both the EEG and GSR signal are sub-divided into non-overlapping windows of 1 sec duration for further analysis. The window length of 1 sec is considered owing to the short term stationary of the signals.

According to an embodiment of the disclosure, the processor 112 further configured to perform the power spectral analysis of the EEG signal. The power spectral analysis is performed to detect a first set of inactive state of the person from the baseline interval and the rest interval. The data while the participant is at rest was used to derive information about inactive state. The frequency band energies as features were used as given in equation below:

$$F=(E\alpha, E\theta)$$

where, the terms correspond to the energies in different frequency bands, i.e. alpha ($E^\alpha$ as 7.5-12.5 Hz), and theta ($E^\theta$ as 4-7.5 Hz) respectively. The energy in each band is calculated using Fast Fourier Transform (FFT) method. Since the working brain can be characterized with the alpha-theta bands, a simple metric was developed to validate this in rest and working states, i.e.

$$f(E^\alpha, E^\theta) = \begin{cases} P_{in_i} = 1, P_{a_i} = 0; E_i^\alpha > E_i^\theta \\ P_{in_i} = 0, P_{a_i} = 1; \text{otherwise} \end{cases}$$

where i=1, 2, 3, . . . , N number of windows for $E^\alpha$ and $E^\theta$ band energies; and $P_{in}$ and $P_a$ represents the presence of inactivity and activity, respectively in a given window. This metric is derived for rest, baseline and the stimulus segments. Next the percentage of windows corresponding to active state in a given task, called the activity measure A, is calculated as shown in equation below:

$$\text{Activity Measure}(A) = \frac{1}{N}\sum_{i=1}^{N} P_{a_i} \times 100$$

Conversely, the % of inactive windows in the given task, referred to as the inactivity measure I, is calculated as below:

$$\text{Inactivity measure}(I) = \frac{1}{N}\sum_{i=1}^{N} P_{in_i} \times 100$$

Let $N_W$ and $N_R$ be the total number of windows in working and rest tasks, respectively. Then following equation depicts that the percentage of active state windows compared to the inactive state windows is expected to be higher in the working segment:

$$\frac{1}{N_W}\sum_{i=1}^{N_W} P_{a_i} \times 100 \gg \frac{1}{N_W}\sum_{i=1}^{N_W} P_{in_i} \times 100$$

In contrast to this, for the rest segment it is expected that the majority of the windows would be in inactive state as follows:

$$\frac{1}{N_R}\sum_{i=1}^{N_R} P_{in_i} \times 100 \gg \frac{1}{N_R}\sum_{i=1}^{N_R} P_{a_i} \times 100$$

These are the basis for using the inactive state as a parameter while deriving the cognitive load. It is to be noted that rejecting the inactive portions from the recorded data is not a good idea as it results in substantial data loss. On the other hand, its inclusion degrades the overall results. Therefore, the need is to enhance the results by retaining both the active and inactive portions.

According to an embodiment of the disclosure, the processor 112 is further configured to identify a most inactive window out of the first set of inactive states. The most inactive window ($B_{rest\_window}$) can be calculated by following equation:

$$B_{rest\_window} = \underset{t \in N}{\mathrm{Argmax}}(E_i^\alpha - E_i^\theta)$$

where, N is the total number of windows in the rest period. In an embodiment of the disclosure, closed eye rest acts as a modified baseline for the activities of the brain and any local task related changes from this baseline are attributed to the functional deactivation or activation corresponding to a well-defined stimulus or experimental condition. This ensures arousal of least thoughts in the brain and absence of eye blinks and least muscle movements.

According to an embodiment of the disclosure, the processor 112 also configured to determine the cognitive load of the person using the EEG signal of the person during the trial state and by using the most inactive window as the modified baseline. Here, both the stimulus and baseline signals are decomposed into the time-frequency domain using S-transform. Next, the mean frequencies and power at that particular frequency are calculated. Then the change in the product of mean frequency and power in both alpha and theta between stimulus and modified baseline is calculated. The calculation is done in a window basis. A window of duration 1 sec is taken. The cognitive load is calculated using following equation:

$$L(n) = \Delta |f_n(\alpha)| f_n(\alpha) - \Delta |f_n(\theta)| f_n(\theta)$$

where $\Delta |f_n(\omega)|$ and $|f_n(\omega)|$ correspond to the change in power and change in mean frequency respectively, between stimulus and baseline for the $n^{th}$ window and ω corresponds to the frequency bands.

According to an embodiment of the disclosure, the processor 112 is also configured to validate the identification of the first inactive window. Initially the power spectral analysis of the GSR signal is performed to determine a second set of inactive state of the person from the baseline interval and the rest interval. It is then followed by identifying the most inactive window out of the set of second inactive states. The most inactive window is during the rest interval of the person.

It should be appreciated that the validation further comprising calculating the time difference between the windows corresponding to the most inactive states derived from EEG signal and GSR signal. This time difference should lie within a predefined threshold, as there is a time lag between EEG signal and GSR signal.

According to another embodiment of the disclosure, the cognitive load derived from EEG signal using the most inactive window derived from the first set of inactive states, for both the low load and the high load task should follow the same trend as GSR spectral power derived from trial states while comparing with the most inactive window derived from the second set of inactive states. The system 100 is also configured to validate the high load task and the low load task, using the most inactive windows derived from the EEG signal and the GSR signal.

The GSR signal measures the variation of electrical potential of the skin. When the body experiences stress, temperature variation etc. the sympathetic nervous system (SNS), a major subunit of human nervous system, increases pseudo-motor innervations, causing electro dermal activity to rise and perspiration to start. GSR is analyzed by extracting two components from the raw signal: slow varying tonic and fast varying phasic component. The tonic component of GSR gives a good measure of the participant's activity state. The components corresponding to the frequencies less than 0.5 Hz are considered as tonic components and the remaining are considered as the phasic component. To compute these components, an N point Fast Fourier transform (FFT) was performed on the complete signal where N is the total number of samples in the signal as given in the equation below:

$$f = \frac{f_s \times k}{N}$$

Here, f is signal frequency, $f_s$ is the sampling frequency and k=1, 2, 3, . . . , N−1. Frequency f was set to 0.5 Hz and the value of k was computed. Let at f=0.5 Hz, k=kT. Next the tonic component (TC) is computed by taking the inverse Fourier transform of the first kT fourier coefficients of the original GSR signal as given in equation below whereas the phasic component (PC) is calculated by taking inverse Fourier transform of the higher Fourier coefficients (kT+1 to N−1) of the original GSR signal as given in equation below:

$$TC = IFFT\left(\sum_{k=0}^{k_T} x(k)e^{-j(\frac{2\pi}{N})nk}\right) \quad PC = IFFT\left(\sum_{k=k_T+1}^{N-1} x(k)e^{-j(\frac{2\pi}{N})nk}\right)$$

The tonic power reflects the amount of activity during a task. It is expected that lower the tonic power, more is the inactivity and vice-versa.

Figure 3:
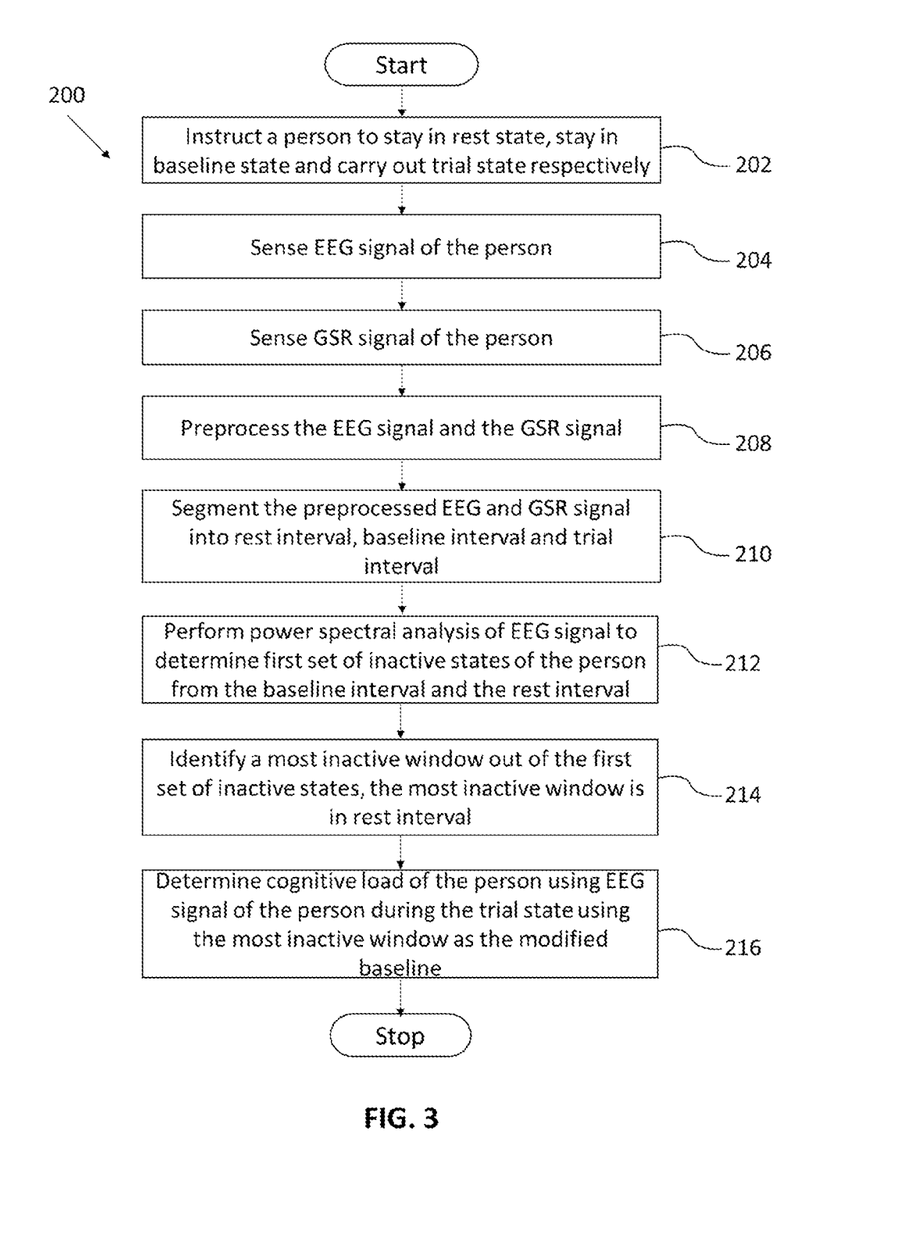
FIG. 3 is a flowchart illustrating the steps involved for determining the cognitive load of a person using a modified baseline, in accordance with an embodiment of the disclosure

In operation, a flowchart 200 for determining the cognitive load of a person using a modified baseline is shown in FIG. 3. Initially at step 202, the person is instructed to stay in an eye closed rest state, stay in a baseline state and carry out a trial state respectively. A task is performed by the person during the trial state. Normally the task includes two types of test, i.e. a low load test and a high load test. At step 204, an EEG signal of the person is sensed using the EEG sensor 104. And at step 206, the GSR signal of the person is sensed using the GSR sensor 106. The GSR signal and the EEG signal are sensed simultaneously when the person is in above mentioned states. At step 208, the EEG signal and the GSR signals are preprocessed using the preprocessor 108.

At the next step 210, the preprocessed EEG signal and the preprocessed GSR signals are in to a rest interval corresponding to the eye closed rest state, a baseline interval corresponding to the baseline state and a trial interval corresponding to the trial state. At step 212, power spectral analysis of the EEG signal is performed to determine a first set of inactive states of the person from the baseline interval and the rest interval.

At the next step 214, the most inactive window is identified out of the first set of inactive states. The most inactive window is during the rest interval of the person. In the present embodiment, the closed eye rest acts as a 'baseline' for the activities of the brain and any local task related changes from this baseline are attributed to the functional deactivation or activation corresponding to a well-defined stimulus or experimental condition. And finally at step 216, the cognitive load of the person is determined using the EEG signal of the person during the trial state and by using the most inactive window as the modified baseline.

According to an embodiment of the disclosure, the use of closed eye rest state as the modified baseline can be validated with the help of following experimental findings. The experiments were performed on the twenty participants (with age groups: 24-30 years). They were selected from a research lab for the study (10 males and 10 females). They are all right handed and are devoid of any mental or physical ailments. All the participants have normal or corrected to normal vision using glasses. They all hail from similar educational and professional backgrounds. These factors are taken into consideration in order to ensure minimal variance in brain lateralization across the participants. The experimentation is carried out in a closed room to avoid any external sound or disturbances.

Figure 4:
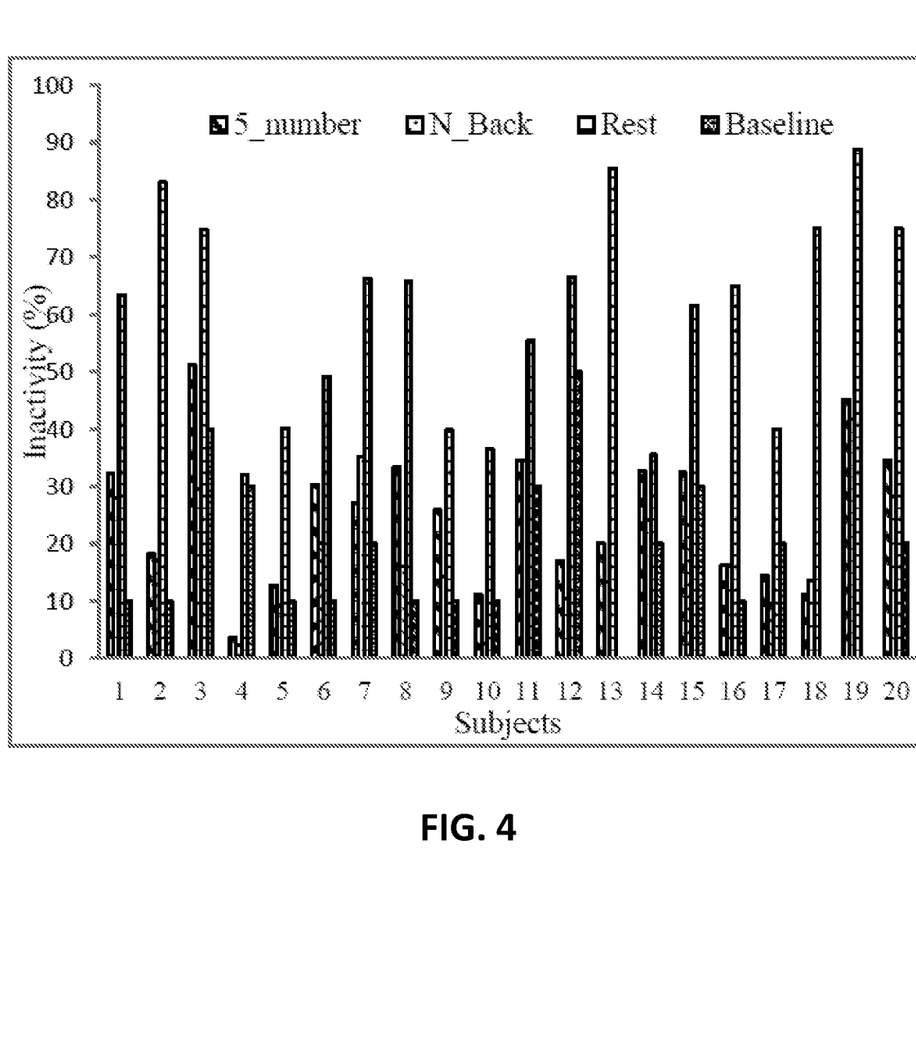
FIG. 4 shows the graphical representation of measure of inactivity in the participants, in accordance with an embodiment of the disclosure.

Using the EEG signals, the metric of inactivity was prepared in each of the 4 tasks (rest, baseline and 2 stimuli) as shown in FIG. 4. It is seen that this metric value is comparatively high in the rest task which is indicative of its ability to better distinguish working and inactive states of the brain. It is to be noted that the percentage of inactive windows in the baseline is comparatively lesser than in the rest state. The tonic power was calculated from GSR data as this component reflects clear separation between the active and inactive states of brain for maximum number of participants. Table 1 reports the minimum value of tonic power for each stimulus. Out of 20 participants, 19 participants' data is presented as the GSR data for S6 is corrupted due to erroneous connection. It is to be noted that for most of the subjects, the minimum of tonic power for the 5-number task was lesser than that corresponding to the 3-back test. These values are also considerably higher than the ones corresponding to the rest state. Thus it can be inferred that the min tonic power is less during the rest state compared to the working states and increases with increase in difficulty level of a task. The data with underline indicates the subjects for whom reverse results are obtained.

The cognitive load from EEG signal is computed using the conventional method (using baseline) and the proposed method (using rest) for both 5-number task and the 3-back task and is compared window-wise, designated as discriminative index (d) as given in following equation:

$$d_i = \begin{cases} 1, & CL_{High_i} > CL_{Low_i} \\ 0, & \text{otherwise} \end{cases}$$

where $CL_{High}$ and $CL_{Low}$ is the cognitive load in high and low load task, respectively in the $i^{th}$ window computed as mentioned above. The time duration in both the tasks—5-number and 3-back are the same and hence the CL values in each window was compared for both the tasks. The total discriminative index (TDI) is the percentage of windows of CL that are high in 3-back when compared to 5-number task and is given in following equation:

$$TDI_k = \frac{1}{N} \sum_{i=1}^{N} d_i \times 100$$

where i=1, 2, 3, ..., N are the number of windows. The k=1 and k=2 indicate the conventional method (using baseline) and the proposed method (using rest), respectively. Higher the values of $TDI_k$, better is the performance. For each subject, the values of TDI are given in Table 1 (EEG results). For most of the participants, $TDI_2$ is higher compared to $TDI_1$. For few participants, reverse trend is observed and marked in underline. This provides a good avenue for sensor fusion. It is to be noted that for subjects S1, S4 and S5, both the EEG and GSR sensor signals generate reverse results (shown in bold underline). A single factor ANOVA is conducted to test whether the two methods (k=1, 2) are similar (null hypothesis). The null hypothesis is rejected as the F value=51.85 is greater than the $F_{cric}$=4.09 with p-value as $1.14 \times 10^{-08}$.

TABLE 1

| Participants | Measure of inactitity (GSR min tonic power) | | | Discriminative index or CL (EEG) | |
| --- | --- | --- | --- | --- | --- |
| | Rest | 5-number | 3-back | TDI$_1$ | TDI$_2$ |
| S1 | 2.0 | 3.1 | 2.1 | 58.92 | 57.67 |
| S2 | 25.6 | 28.3 | 29.5 | 8.6 | 45.86 |
| S3 | 23.4 | 34.0 | 43.2 | 18.03 | 59.42 |
| S4 | 3.9 | 10.9 | 3.8 | 60.49 | 51.44 |
| S5 | 0.9 | 1.2 | 0.9 | 80.83 | 63.33 |
| S6 | — | — | — | 33.57 | 60.14 |
| S7 | 3.8 | 4.8 | 4.5 | 36.36 | 40.15 |
| S8 | 6.7 | 1.3 | 1.6 | 49.23 | 56.1 |
| S9 | 22.7 | 41.2 | 74.6 | 10.92 | 92.43 |
| S10 | 0.7 | 1.0 | 3.1 | 60.68 | 69.23 |
| S11 | 29.1 | 15.1 | 23.7 | 38.79 | 76 |
| S12 | 49.1 | 75.7 | 87.7 | 52.58 | 72.41 |
| S13 | 16.9 | 5.1 | 13.8 | 70.58 | 75.6 |
| S14 | 40.6 | 61.7 | 82.6 | 95.68 | 96.55 |
| S15 | 13.2 | 3.8 | 8.4 | 33.62 | 63.79 |
| S16 | 13.3 | 42.9 | 55.0 | 80.34 | 82.05 |
| S17 | 21.2 | 24.4 | 120.0 | 95.72 | 97.43 |
| S18 | 13.1 | 16.1 | 10.9 | 52.13 | 65.81 |
| S19 | 30.2 | 118.1 | 129.0 | 28.2 | 45.29 |
| S20 | 131.6 | 235.7 | 337.9 | 80.17 | 86.2 |

Figure 5:
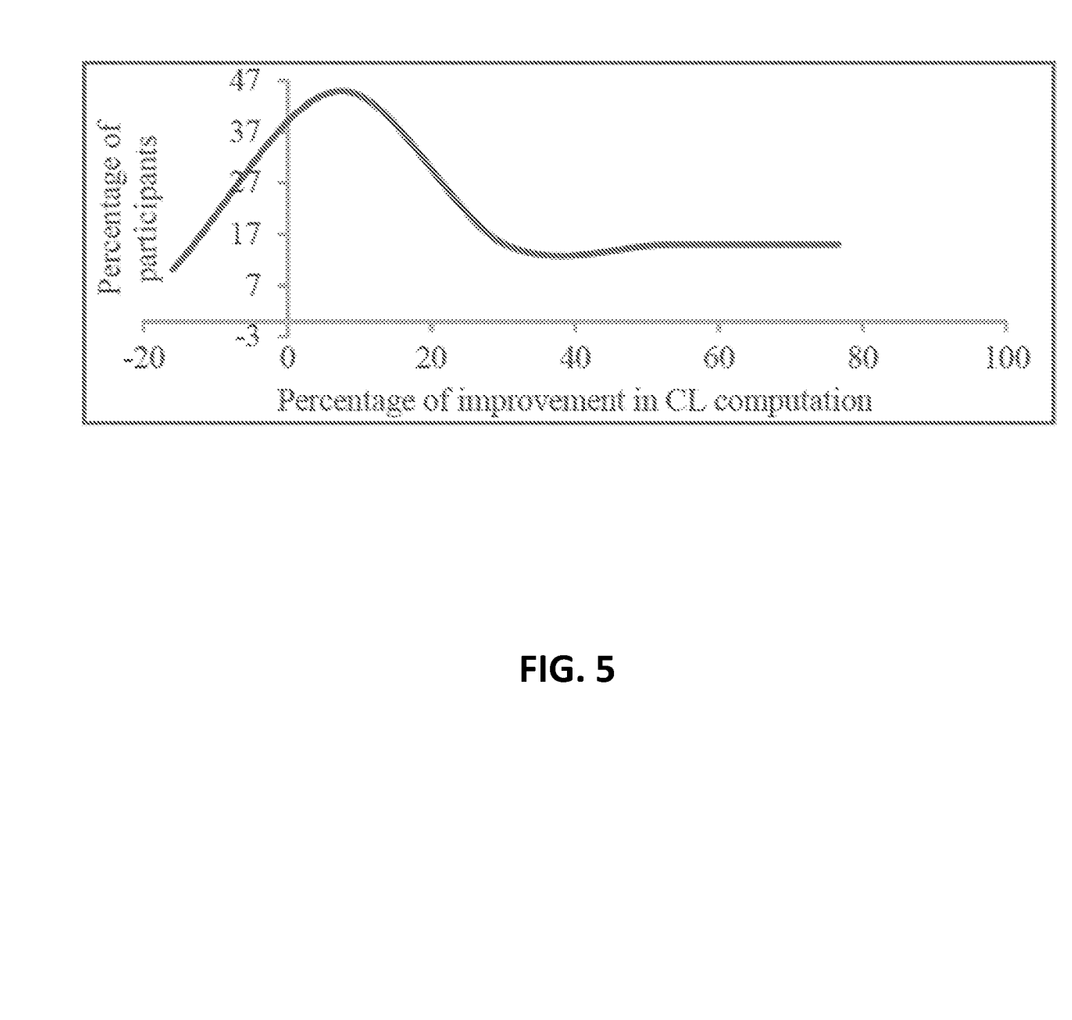
FIG. 5 shows the histogram of the cognitive load enhancement, in accordance with an embodiment of the disclosure.

A histogram analysis is performed on the difference between $TDI_2$ and $TDI_1$ as shown in FIG. 5. It is to be noted that though there are few percentage of participants for whom the CL detection is reverse (higher CL for easy stimulus and vice-versa), there is considerable amount of improvement for the majority of participants. The proposed method performs better in comparison to its counterpart by an average of 15.57%.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims. The embodiment, thus provides the system and method for measuring cognitive load of the person using a modified baseline derived by determining the inactive state from the rest state of the person.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments may include a hardware configuration of an information handling/computer system in accordance with the embodiments herein. The system herein comprises at least one processor or central processing unit (CPU). The CPUs are interconnected via system bus to various devices such as a random access memory (RAM), read-only memory (ROM), and an input/output (I/O) adapter. The I/O adapter can connect to peripheral devices, such as disk units and tape drives, or other program storage devices that are readable by the system. The system can read the inventive instructions on the program storage devices and follow these instructions to execute the methodology of the embodiments herein.

The system further includes a user interface adapter that connects a keyboard, mouse, speaker, microphone, and/or other user interface devices such as a touch screen device (not shown) to the bus to gather user input. Additionally, a communication adapter connects the bus to a data processing network, and a display adapter connects the bus to a display device which may be embodied as an output device such as a monitor, printer, or transmitter, for example. The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

What is claimed is:

1. A method for determining a cognitive load of a person using a modified baseline, the method comprising a processor implemented steps of:

instructing the person to stay in an eyes closed rest state, stay in a baseline state and carry out a trial state respectively, wherein, a task is performed by the person during the trial state;

sensing an Electroencephalogram (EEG) signal of the person using an EEG sensor;

sensing a Galvanic Skin Response (GSR) signal of the person using a GSR sensor;

preprocessing the EEG signal and the GSR signal using a preprocessor;

segmenting the preprocessed EEG signal and the preprocessed GSR signal into a rest interval corresponding to the rest state, a baseline interval corresponding to the baseline state and a trial interval corresponding to the trial state;

performing power spectral analysis of the EEG signal to determine a first set of inactive states of the person from the baseline interval and the rest interval;

identifying a most inactive window out of the first set of inactive states, wherein the most inactive window is during the rest interval of the person;

determining the cognitive load of the person using the EEG signal of the person during the trial state and by using the most inactive window as the modified baseline; and validating the identification of the first inactive window, wherein validating comprises:

performing power spectral analysis of the GSR signal to determine a set of second inactive states of the person from the baseline interval and the rest interval;

identifying a most inactive window out of the set of second inactive states, wherein the most inactive window is during the rest interval of the person; and validating the most inactive state derived from the EEG signal with respect to the most inactive state derived from the GSR signal.

2. The method of claim 1, wherein the task includes a high load task and a low load task.

3. The method of claim 1 further comprising validating the high load task and the low load task, using the most inactive windows derived from the EEG signal and the GSR signal.

4. The method of claim 1 further comprises of sub dividing the preprocessed EEG signal and the preprocessed GSR signal into windows of 1 second duration.

5. The method of claim 1, wherein the step of determining the cognitive load further comprises:

decomposing the EEG signal into a time frequency domain using S Transform;

calculating a mean frequency and power of the decomposed EEG signal at various frequencies;

calculating change in product of the mean frequency and the power in both alpha range of 8-12 Hz and theta range of 4-7 Hz of the EEG signal between the stimulus interval and the rest interval; and calculating the cognitive load using the change in the product of the mean frequency and the power in each of the windows.

6. The method of claim 1, wherein the power spectral analysis of the EEG signal further comprises:

determining energies of a plurality of frequency bands of the EEG signal using Fast Fourier Transform;

creating a metric of energies to validate in the rest state, conventional baseline state and the trial state, wherein the metric comprises of presence of inactivity and presence of activity in the window; and calculating an activity measure corresponding to the activity state and an inactivity measure corresponding to the inactivity state of the person.

7. The method of claim 1, wherein the power spectral analysis of the GSR signal further comprises extraction of tonic component and phasic component of the GSR signal, wherein the tonic component is indicative of the inactive state of the person.

8. The method of claim 1, wherein in the rest state of the person is resting with eyes closed.

9. A system for determining a cognitive load of a person using a modified baseline, the system comprises:

an input/output interface for instructing the person to stay in an eyes closed rest state, stay in a baseline state and carry out a trial state respectively, wherein, a task is performed by the person during the trial state;

an Electroencephalogram (EEG) sensor for sensing an EEG signal of the person;

a Galvanic Skin Response (GSR) sensor for sensing a GSR signal of the person;

a preprocessor for preprocessing the EEG signal and the GSR signal;

a memory; and a processor coupled with the memory, wherein the processor further configured to perform the steps of:

segmenting the preprocessed EEG signal and the preprocessed GSR signal into a rest interval corresponding to the rest state, a baseline interval corresponding to the baseline state and a trial interval corresponding to the trial state;

performing power spectral analysis of the EEG signal to determine a first set of inactive states of the person from the baseline interval and the rest interval;

identifying a most inactive window out of the first set of inactive states, wherein the most inactive window is during the rest interval of the person;

determining the cognitive load of the person using the EEG signal of the person during the trial state and by using the most inactive window as the modified baseline; and validating the identification of the first inactive window, wherein validating comprises:

performing power spectral analysis of the GSR signal to determine a set of second inactive states of the person from the baseline interval and the rest interval;

identifying a most inactive window out of the set of second inactive states, wherein the most inactive window is during the rest interval of the person; and validating the most inactive state derived from the EEG signal with respect to the most inactive state derived from the GSR signal.

10. A non-transitory computer readable medium embodying a program executable in a computing device for determining a cognitive load of a person using a modified baseline, the program comprising a processor implemented steps of:

instructing the person to stay in an eyes closed rest state, stay in a baseline state and carry out a trial state respectively, wherein, a task is performed by the person during the trial state;

sensing an Electroencephalogram (EEG) signal of the person using an EEG sensor;

sensing a Galvanic Skin Response (GSR) signal of the person using a GSR sensor;

preprocessing the EEG signal and the GSR signal using a preprocessor;

segmenting the preprocessed EEG signal and the preprocessed GSR signal into a rest interval corresponding to the rest state, a baseline interval corresponding to the baseline state and a trial interval corresponding to the trial state;

performing power spectral analysis of the EEG signal to determine a first set of inactive states of the person from the baseline interval and the rest interval;

identifying a most inactive window out of the first set of inactive states, wherein the most inactive window is during the rest interval of the person;

determining the cognitive load of the person using the EEG signal of the person during the trial state and by using the most inactive window as the modified baseline; and validating the identification of the first inactive window, wherein validating comprises:

performing power spectral analysis of the GSR signal to determine a set of second inactive states of the person from the baseline interval and the rest interval;

identifying a most inactive window out of the set of second inactive states, wherein the most inactive window is during the rest interval of the person; and validating the most inactive state derived from the EEG signal with respect to the most inactive state derived from the GSR signal.

* * * * *